United States Patent [19]

Lekholm et al.

[11] Patent Number: 4,869,251
[45] Date of Patent: Sep. 26, 1989

[54] IMPLANTABLE HEART PACEMAKER WITH A SENSOR FOR INERTIAL AND/OR ROTATIONAL MOVEMENTS OF THE USER

[75] Inventors: Anders Lekholm, Bromma; Gösta Säll, Norsborg; Liliane Wecke, Solna; Kurt Högnelid, Sundbyberg, all of Sweden

[73] Assignee: Siemens Aktiengesellschaft, Berlin and Munich, Fed. Rep. of Germany

[21] Appl. No.: 192,609

[22] Filed: May 11, 1988

Related U.S. Application Data

[62] Division of Ser. No. 72,170, Jul. 10, 1987.

[30] Foreign Application Priority Data

Jul. 15, 1986 [DE] Fed. Rep. of Germany ....... 3623905

[51] Int. Cl.$^4$ .......................... A61N 1/00; H05G 00/00
[52] U.S. Cl. .............................. 128/419 PG
[58] Field of Search .................... 128/419 P, 419 PG; 73/654, 514, 517 R; 340/669

[56] References Cited

U.S. PATENT DOCUMENTS

| | | | |
|---|---|---|---|
| 2,979,959 | 4/1961 | Clurman | 73/516 R |
| 3,129,347 | 4/1964 | Tognola | 310/15 |
| 3,486,506 | 12/1969 | Auphan | 128/419 P |
| 3,554,199 | 1/1971 | Auphan | 128/419 PG |
| 3,619,524 | 11/1971 | Gillund | 200/61.45 M |
| 3,926,198 | 12/1975 | Kolenik | 128/419 PG |
| 4,031,848 | 6/1977 | Killen | 116/200 |
| 4,527,153 | 7/1985 | Suzuki et al. | 340/572 |
| 4,771,780 | 9/1988 | Sholder | 128/419 PG |

FOREIGN PATENT DOCUMENTS

| | | | |
|---|---|---|---|
| 0080348 | 1/1983 | European Pat. Off. | 128/419 PG |
| 83/00218 | 1/1983 | World Int. Prop. O. | 73/514 |

OTHER PUBLICATIONS

"How to Measure Anything With Electronic Instruments," Kueken, 1981, pp. 167–171.

Primary Examiner—Francis Jaworski
Assistant Examiner—George Manuel
Attorney, Agent, or Firm—Hill, Van Santen, Steadman & Simpson

[57] ABSTRACT

A pacemaker has a sensor for detehing inertial and/or rotational movements of a patient in whom the pacemaker is implanted. The sensor has a hollow member with at least one freely moveable member therein, the freely moveable member generating a mechanical vibration upon movement thereof within the hollow member caused by movement or rotation of the patient. A transducer generates an electrical signal corresponding to the mechanical vibrations, the electrical signal being proportional to the movement. This electrical signal is used to vary the rate at which stimulation pulses are supplied to the patient by the pacemaker.

33 Claims, 7 Drawing Sheets

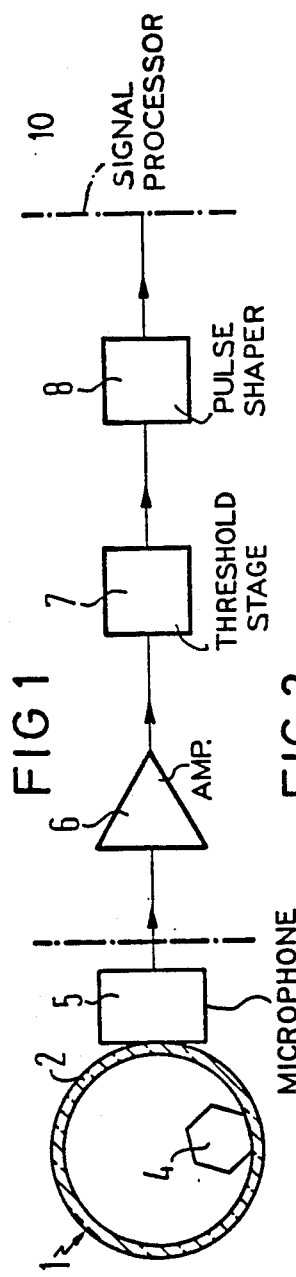
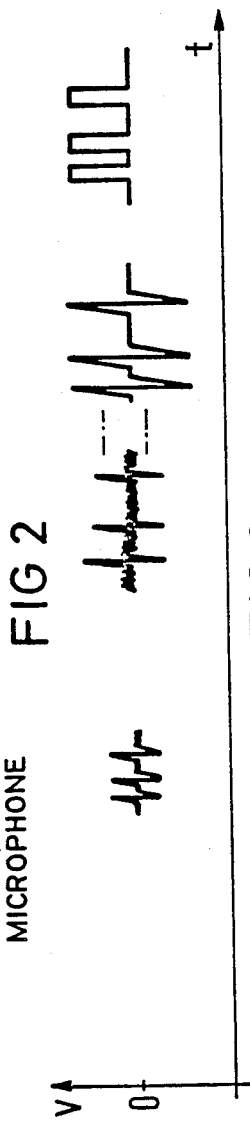
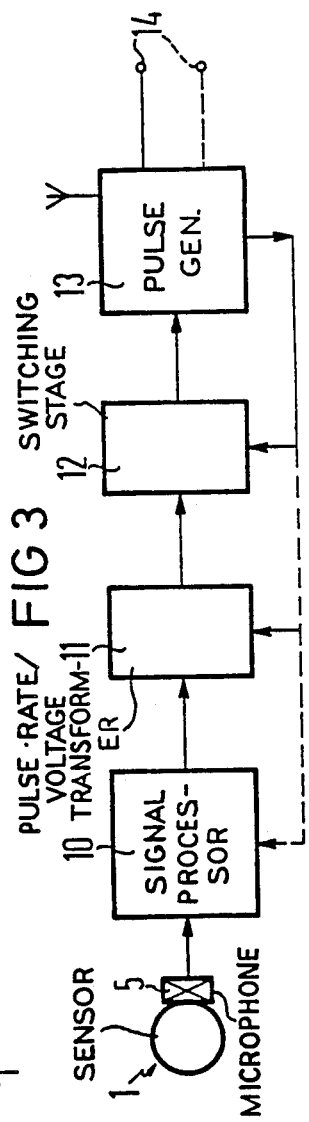

IMPLANTABLE HEART PACEMAKER WITH A SENSOR FOR INERTIAL AND/OR ROTATIONAL MOVEMENTS OF THE USER

This is a division of application Ser. No. 072,170, filed 7/10/87.

BACKGROUND OF THE INVENTION

1. Field of the Invention

The present invention is directed to a sensor for inertial and/or rotational movements of an object or a life form, in particular to a sensor for movements of a human subject.

2. Description of the Prior Art

It is desireable to control the pacing rate of heart pacemakers in dependence upon selected physiological parameters which are a measure of the physical activity of the patient. A pacemaker of this type is known, for example, in U.S. Pat. No. 4,428,378, wherein a microphone is used as a sensor.

In such conventional devices, however, a number of unwanted signals are acquired simultaneously with the signals corresponding to the activity of interest, such unwanted signals, for example, resulting from respiratory and cardiac noises or noises deriving from sources outside of the patient. The disturbances picked-up by conventional sensors are also dependent on the physical characteristics of the patient, i.e., on the corpulence or muscularity of the patient, so that relatively complex sensitivity adjustments differing from patient to patient with different noise suppression characteristics must be undertaken.

SUMMARY OF THE INVENTION

It is an object of the present invention to provide a sensor for inertial and/or rotational movements of an object or life form which is universally employable and which can be adapted to a great variety of applications with simple modifications.

It is a further object of the present invention to provide such a sensor which is specifically suitable for use in an implantable heart pacemaker.

The above objects are achieved in accordance with the principles of the present invention in a sensor having a hollow member in which at least one element is disposed in a freely mobile fashion, with a transducer disposed at or sufficiently close to the hollow member to acquire mechanical vibrations caused by relative movements between the hollow member and the mobile element and for converting the mechanical vibrations into an electrical signal which is at least partially proportional to the movement.

The freely moveable element is preferably a geometrically regular element, such as a regular polyhedron made of a hard material. The element in another embodiment may be a sphere, with the interior of the hollow member being facetted.

For the purpose of a general explanation of the functioning of the sensor, an example will be assumed wherein the hollow member has a spherical interior, and the moveable element is an icosahedron or a dodecahedron. When the object or life form whose inertial or rotational movements are to be identified is at rest, the moveable element will lie on one of its faces against the interior of the hollow member. When the hollow member is subjected to forces due to acceleration or rotation, the moveable element will move together with the hollow member until the center of gravity of the moveable element reaches the edge of the surface on which it is resting. Further rotation or acceleration will cause the moveable element to roll onto an adjacent face, where a new equilibrium condition will occur. A mechanical concussion or vibration is generated during the roll of the moveable element onto the new face. This concussion can be heard as a clicking sound, and is acquired by a transducer, such as a microphone. In another embodiment, however, the moveable element may be a permanent magnetic dipole, and the transducer may be one or more coils arranged around the hollow member, with a current being generated in the coils when the moveable element changes position in the interior of the hollow member.

The movements of the moveable element are "quantized" on the basis of the shape of the moveable element and the shape of the hollow member. When the moveable element moves relative to the hollow member, it produces a combination of signals consisting of noise produced by sliding movement of the moveable element and clicking noises produced by rolling movement of the moveable element. After amplification, for example, the signals obtained by the transducer can be processed by a threshold circuit and a pulse shaper, so that uniform pulses of identical amplitude and width are generated, each pulse corresponding to the shift of the moveable element from one face to another. The signal generated in this manner, i.e., the frequency of these pulses, can then be used as a measure for the intensity of the acceleration or rotational movement to which the sensor is exposed.

If the interior wall of the hollow member consists of elastic material, the concussion excited by the moveable element will cause damped mechanical oscillations. The frequencies of these oscillations is defined by the mechanical properties, i.e., the elasticity, of the inside wall of the hollow member. Detection of such oscillations using a narrow-band amplifier results in a high supression of unwanted signals.

Preferably the sensitivity of the sensor can be varied in a simple manner by varying the structure of the sensor, without any loss in the accuracy of the measurement.

In a further embodiment of the invention the sensitivity of the sensor is different in different directions and/or positions (attitudes). For example, such sensitivity can be achieved by modifying the shape of the hollow member from spherical (isotropic sensitivity) to ellipsoid. Another simple way to accomplish such anisotropic sensitivity is to manufacture certain portions of the hollow member of a softer material than others. Such directional sensitivity can also be achieved by using a spherical hollow member with selected portions of the inner surface of the hollow member being smooth, and other portions being facetted. The signal amplitudes produced in such directional structures are sufficiently different to enable signal processing circuitry to suppress signals corresponding to movement of the moveable element at specific locations within the hollow member, or in specific directions. In an extreme case, the sensor can be made insensitive for movements in specific positions or directions.

The sensitivity of the sensor can also be varied by varying the relative size of the hollow member in relationship to the size of the moveable element, or by modifying the shape of one of these components. For example, an icosahedron will roll more easily than a cube. The highest sensitivity is achieved in an embodiment wherein the moveable element is a small ball disposed within a large spherical hollow member. Because the mechanical vibrations in this embodiment are extremely small, and may even be zero under ideal conditions, the moveable element is a permanent magnet and a magnetic transducer is used to monitor the movement thereof.

Movements of the moveable element within the hollow member can be selectively influenced by filling the interior of the hollow member with a fluid of selected viscosity, or by filling the interior with a plurality of particles which produce additional detectable pressure waves or signals as a result of their collective movement against the inside wall of the hollow member or against one another. A combination of a fluid and plurality of particles can also be used.

The sensor disclosed herein can be used in an implantable heart pacemaker having a pulse generator which generates variable frequency stimulation pulses. The physical activity of a patient in which the pacemaker is implanted is monitored using the sensor, and the output signal of the sensor is used to control the frequency of the pulse generator. The use of such a sensor for frequency control of an implantable heart pacemaker has a number of advantages over known devices. The sensor forms an entirely self-contained system within the heart pacemaker, which requires no additional external detectors or line connections outside of the heart pacemaker housing. Moreover, the sensor can be precisely calibrated for accelleration or for rotational movements in a range which corresponds to the normal activities of a patient. The sensor thus does not have to be individually adapted for each patient. A single adaptation which would possibly be required would be an adjustment of the transfer function used to form the frequency control signal for the pulse generator, such that a specific activity would result in an optimum stimulation frequency for each patient.

DESCRIPTION OF THE DRAWINGS

FIG. 1 is a schematic block diagram of a sensor and processing circuitry constructed in accordance with the principles of the present invention.

FIG. 2 is a voltage/time diagram showing the signals at the respective outputs of the components of FIG. 1.

FIG. 3 is a schematic block diagram of a sensor constructed in accordance with the principles of the present invention in a frequency-controlled pacemaker.

DESCRIPTION OF THE PREFERRED EMBODIMENTS

Figure 4:
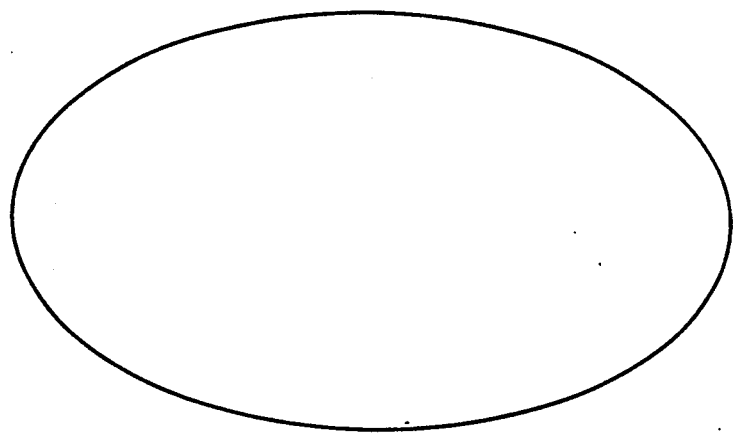
FIGS. 4, 5 and 6 show various views of an ellipsoid embodiment of the hollow member of a sensor constructed in accordance with the principles of the present invention.

A sensor generally referenced at 1, and processing circuitry for the sensor signal, are shown in FIG. 1. The sensor 1 consists of a hollow ball 2 consisting of, for example, glass in which a regular polyhedron 4 consisting of, for example, polished stone, is disposed. A transducer 5, such as a microphone, is disposed at the outside wall of the hollow ball 2, which picks-up noises produced by relative motion between the hollow ball and the polyhedron. The electrical output signal of the transducer 5 is supplied through an amplifier 6 and through a threshold stage 7 to a pulse shaper 8.

The respective signals at the output of the microphone 5, the output of the amplifier 6, the output of the threshold stage 7 and the output of the pulse shaper 8 are shown from left to right in FIG. 2. As can be seen in FIG. 2, sensor pulses having uniform amplitude and pulse width are present at the output of the pulse shaper 8. Only the "clicking" sounds cause by tilting of the polyhedren 4 from one surface to a neighboring surface are indicated at the output.

The use of a sensor 1 as shown in FIG. 1 in combination with control circuitry for a heart pacemaker is shown in FIG. 3. The amplifier 6, threshold stage 7 and pulse shaper 8 of FIG. 1 are incorporated in block 10 of FIG. 3. The output signal from block 10 is supplied to a pulse rate/voltage transformer 11, and the output of the transformer 11 is supplied to a switching stage 12, which converts this activity signal (varying voltage) into a control signal based on an algorithm, this control signal driving a pulse generator 13 of the heart pacemaker. The algorithm for the switch stage 12 can be linear or non-linear. All components of the circuit shown in FIG. 3 may be programmable, so that the control signal can be individually adapted for each patient in accord with the patient's physiological condition. The output signals of the pulse generator 13 are supplied to the patient's heart via one or more lines 14.

The control signal for the heart pacemaker may be generated in digital form instead of the analog format discussed above. Digital processing can be undertaken in a microprocessor. In both cases, the programming can be done via a telemetry connection between the heart pacemaker and an external programming means.

Figure 5:
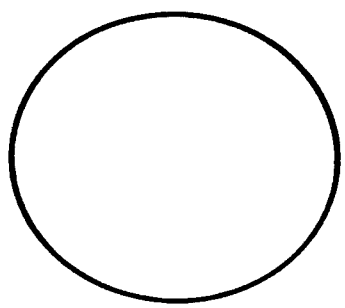
Figure 6:
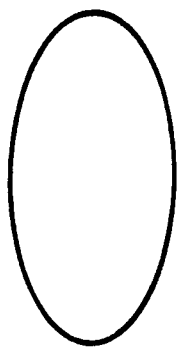

FIGS. 4 through 6 show various views of an ellipsoid hollow member 2a. FIG. 4 is a side view and FIGS. 5 and 6 are respective schematic sections in two perpendicular planes. If a moveable element such as a polyhedron is disposed within the hollow member 2a, the polyhedron will roll from one face to the other with differing ease given identical body activity in dependence upon the degree of curvature of the ellipsoid.

Figure 7:
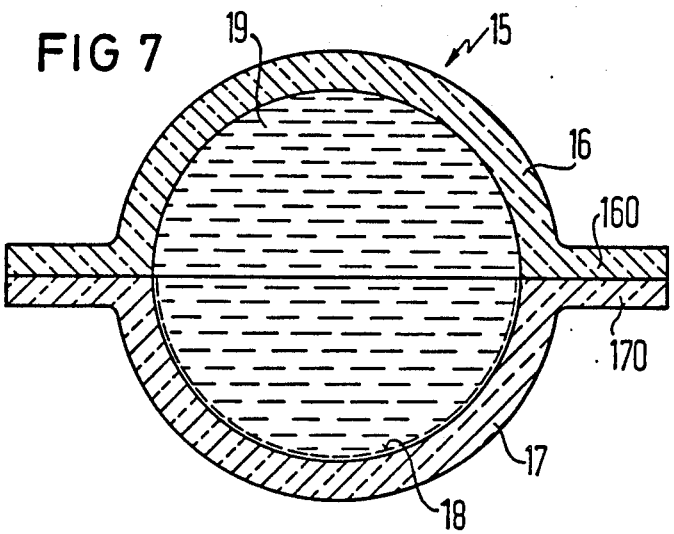
FIG. 7 is a side sectional view of a further embodiment of a sensor constructed in accordance with the principles of the present invention wherein the hollow interior consists of differently textured surfaces, and which may be fluid-filled.

Another embodiment of a sensor constructed in accordance with the principles of the present invention is shown in FIG. 7, wherein the sensor exhibits different sensitivity in different directions. In this embodiment, a spherical hollow member 15 consists of two hemispherical shells 16 and 17. Both shells 16 and 17 may, for example, consist of glass, and the shell 16 may have a smooth interior surface and the shell 17 may have a structured interior surface, as indicated by the dashed line 18. The shells 16 and 17 have respective collars 160 and 170, to permit a tight joining of the two shells.

A polyhedron (not shown) can be used as the moveable element in the embodiment of FIG. 7. As also shown in FIG. 7, the hollow member 15 can be filled with a fluid 19 which damps the relative movements of the polyhedron within the hollow member 15.

Figure 8:
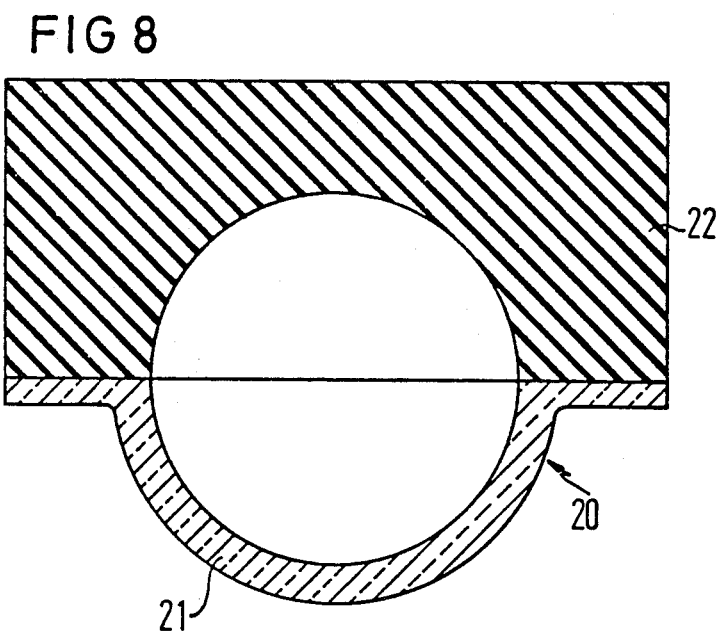
FIG. 8 is a side sectional view of another embodiment of a sensor constructed in accordance with the principles of the present invention wherein portions of the interior surface of the hollow member respectively consists of materials having different mechanical properties.

Another embodiment of a sensor is shown in FIG. 8, which also achieves directed sensitivity. In this embodiment, the sensor 20 consists of two half-shells 21 and 22, with the half-shell 21 consisting of glass and the other half-shell 22 consisting of relatively soft rubber.

In the embodiments of FIGS. 4 through 8, only the hollow member of the sensor has been shown, and the transducer 4 acquiring signals corresponding to the relative movement of the moveable element within the hollow member has been omitted. As in FIG. 1, for example, this transducer may consist of a microphone disposed at or in the proximity of the hollow member.

Figure 9:
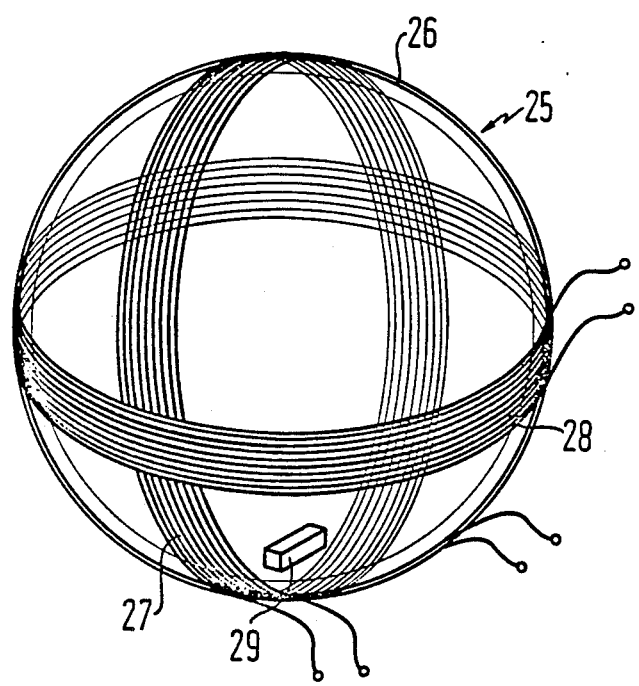
FIG. 9 is perspective view of another embodiment of a sensor constructed in accordance with the principles of the present invention having a magnetic dipole as the moveable element and coils to monitor movement thereof.

An exemplary embodiment is shown in FIG. 9 using a different transducer. For simplicity, a spherical sensor 25 is shown having three orthogonally arranged coils 26, 27 and 28 on the circumference thereof. A magnetic dipole 29 is disposed in the interior of the sensor 25 as the moveable element. Upon relative movement of the magnetic dipole 29, a voltage is induced in the coils 26, 27 and 28.

Figure 10:
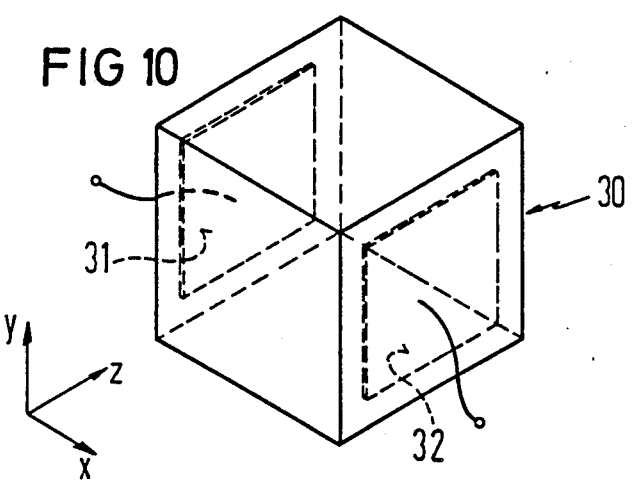
FIG. 10 is a perspective view of another embodiment of a sensor constructed in accordance with the principles of the present invention.
Figure 11:
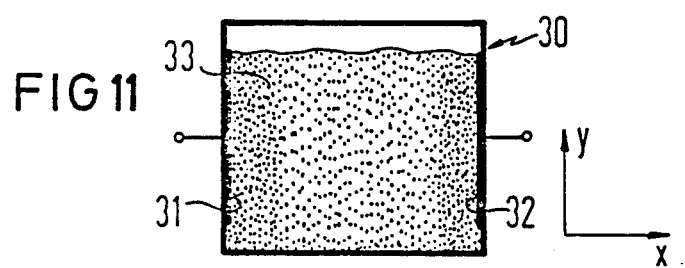
FIGS. 11 and 12 are side sectional views of the sensor of FIG. 10 in different orientations.
Figure 12:
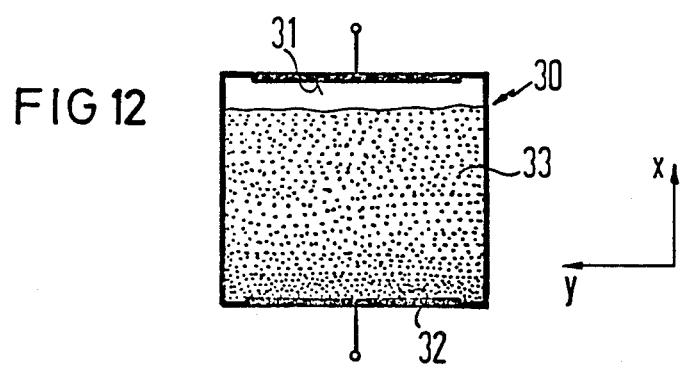

Another embodiment of a sensor constructed in accordance with the principles of the present invention is shown in FIGS. 10 through 12. A three-dimensional illustration of a sensor 30 in the form of a hollow cube is shown in FIG. 10, the inside surfaces of the cube in the y-z plane having respective electrodes 31 and 32 thereon. The interior of the sensor 30 is at least partially loosely filled with electrically conductive particles, such as carbon particles. These particles are not shown in the illustration of FIG. 10, but are shown in FIGS. 11 and 12. For illustrating the orientation of the sensor 30 and for explaining FIGS. 11 and 12, a coordinate system is shown next to the cube in each drawing.

A section through the cube-shaped sensor 30 in the x-y plane is shown in FIG. 7, with the y-axis being vertically oriented. The electrodes 31 and 32 are connected to a voltage source (not shown) similar to a carbon microphone. When force is exerted on the sensor 30 due to movement of the patient or the object in which the sensor is disposed, the carbon particles 33 re-orient, resulting in a change in resistance between the electrodes 31 and 32.

FIG. 12 shows the same section of the cube 30 as in FIG. 11, with the x-axis vertically oriented. As shown in FIG. 12, a layer free of carbon particles 33, and thus electrically insulating, will form between the carbon particles 33 and the upper electrode 31, so that the circuit is substantially open at this position of the sensor 30. The sensor can thus be arranged in a heart pacemaker such that smaller force influences are not detected when the patient is in a prone position.

The sensors shown in FIGS. 10 through 12 are thus directionally dependent in sensitivity. In contrast to normal carbon microphones, a membrane is not deformed due to the action of the force, i.e., the sound waves in a conventional carbon microphone, but rather the size of the cavity filled with the carbon particles is varied. The carbon particles are placed in motion due to the action of the force and re-orient.

Figure 13:
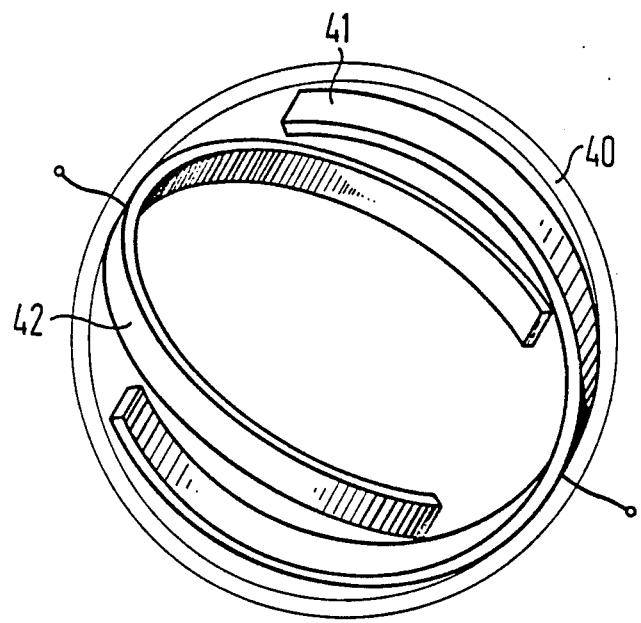
FIG. 13 is a sectional view of a further embodiment of a spherical moveable element for use in a sensor constructed in accordance with the principles of the present invention.

An embodiment of a sensor operating on the same principle as the sensor shown in FIGS. 10 through 12 is shown in FIG. 13, but having isotropic sensitivity. In this embodiment, the hollow member 40 is a sphere and is provided at its interior with two roughly C-shaped electrodes 41 and 42. The hollow member 40 is again loosely filled with conductive particles (not shown).

Figure 14:
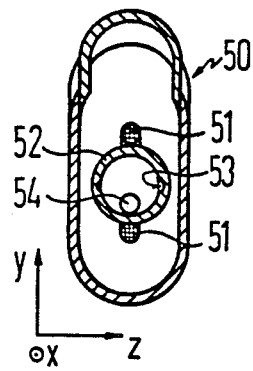
FIGS. 14 and 15 show two sectional views through a heart pacemaker having a sensor therein constructed in accordance with the principles of the present invention.
Figure 15:
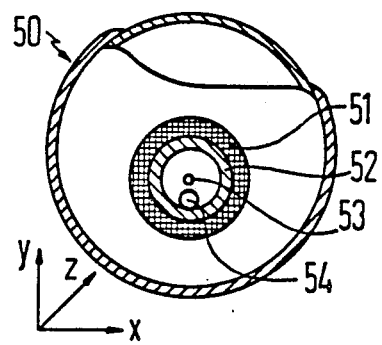
Figure 16:
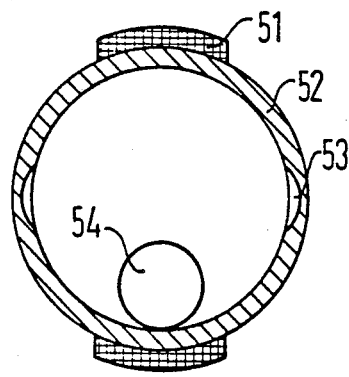
FIGS. 16 and 17 are two sectional views (enlarged) of the sensor constructed in accordance with the principles of the present invention shown in FIGS. 14 and 15.
Figure 17:
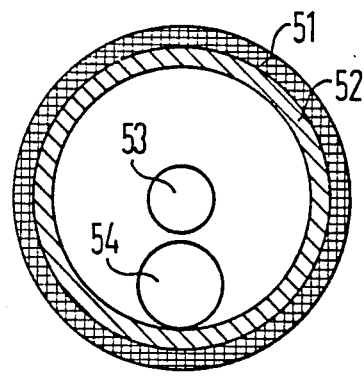

An inductive sensor in an exemplary arrangement of a frequency-controlled heart pacemaker is shown in FIGS. 14 through 17. A schematic side view of the heart pacemaker is shown in FIG. 14, with the sensor integrated therein, and FIG. 15 shows the corresponding front view. The x-y plane in FIGS. 14 and 15 corresponds to the plane in which the heart pacemaker 50 is implanted in a patient. FIG. 16 is a schematic section through the sensor in the orientation of FIG. 14, and FIG. 17 is a schematic front section through the sensor corresponding to the orientation of FIG. 17.

An annular coil 51, consisting of insulated silver/copper wire, is arranged on the spherical hollow member 52. The interior wall of the hollow member 52 has two cavities 53 in the z-direction. The moveable element in this embodiment is a spherical magnetic dipole 54.

The sensor is symmetrical in the x-y plane, and its function is thus not influenced by a possible rotation of the heart pacemaker 50 in the body of the patient. The two cavities 53 are quiescent or rest positions for the spherical dipole 54. For example, when the patient is disposed in a prone position, the cavities 53 result in a threshold for the positional change of the spherical dipole 54 which must be exceeded before the sensor produced frequency increases in the stimulation rate of the pacemaker. The magnetic dipole 54 may consist of a magnetized steel ball or a sintered spherical powder magnet. A non-spherical dipole cast into a sphere may also be used. The sphere may be provided with an outer layer (for example, nickel) to maintain the friction between the interior wall of the hollow member 52 and the sphere 54 stable over a long period. If the spherical dipole 54 consists of sintered material, this layer will also prevent abrasion.

The hollow member 52 may consist, for example, of glass, ceramic, plexiglass, thermoplastic, curable plastic, metal, rubber (for example, silicone rubber) or any other suitable material. As an alternative to a sphere, a blunted sphere, or a cylinder provided with conical terminating covers along the z-axis, may be used.

Figure 18:
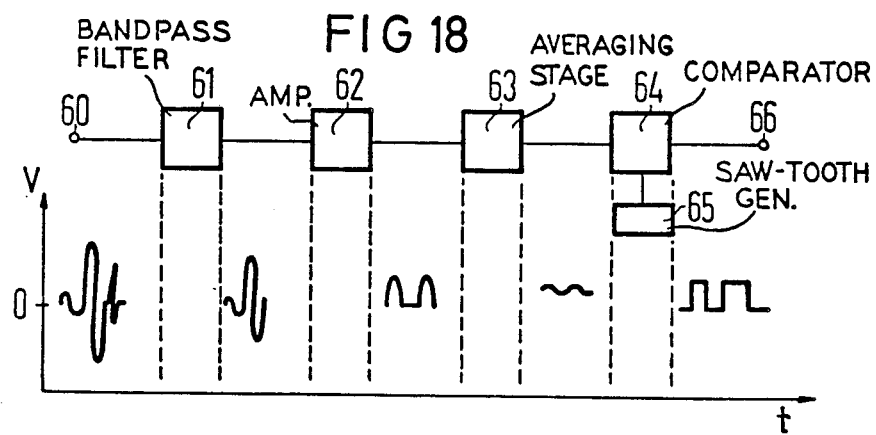
FIG. 18 is a schematic block diagram for control circuitry for the stimulation frequency of the heart pacemaker shown in FIGS. 14 and 15 with a corresponding voltage/time diagram showing the respective signals at various states of the control circuitry.

The various stages of the control electronics, and the signal shapes relating thereto are shown in FIG. 18. An input signal from the sensor is supplied at 60, and has a frequency of about 10 through about 15 Hz. The sensor signal is supplied to a bandpass filter 61 (5 through 25 Hz), followed by a non-linear amplifier stage 62. The output of the amplifier stage 62 is supplied to an averaging stage 63, which may be a capacitor. The output of the averaging stage 63 is supplied to the input of a comparator 64, with a saw-tooth generator 65 being connected to the other input of the comparator 64. The saw-tooth voltage from the generator 65 causes the voltage variation in the output of averaging stage 63 to be converted into a corresponding pulse width variation. The pulse-width modulated signal at the output 66 is then used for control of the heart pacemaker frequency in a known manner.

Although modifications and changes may be suggested by those skilled in the art it is the intention of the inventor to embody within the patent warranted hereon all changes and modifications as reasonably and properly come within the scope of his contribution to the art.

We claim as our invention:

1. A pacemaker implantable in a patient for stimulating the heart of said patient comprising:
   sensing means for detecting physical activity of said patient including a hollow element, freely moveable means enclosed in said hollow element, and means connected to said hollow element for detecting relative movement between said freely moveable means and said hollow element and generating an electrical signal proportional to said movement; and
   means for generating stimulation pulses for stimulating said heart at a stimulation frequency including means responsive to said electrical signal for varying said stimulation frequency dependent on said physical activity of said patient.

2. A pacemaker as claimed in claim 1, further comprising a housing, and wherein said sensing means is disposed within said housing.

3. A pacemaker as claimed in claim 1, wherein said hollow element has an interior surface with at least one cavity therein for receiving said freely moveable means in a rest position, said sensor being adapted to be disposed within said patient such that said freely moveable means is received in said cavity when said patient is in a prone position.

4. A pacemaker as claimed in claim 1, wherein said freely moveable means is a means for generating an acoustic signal when moving relative to said hollow element, and wherein said means for detecting comprises a transducer for receiving said acoustic signal and converting said acoustic signal into said electrical signal.

5. A pacemaker as claimed in claim 1, wherein said freely moveable means constitutes a magnetic dipole, and wherein said means for detecting constitutes a coil disposed such that said relative movement between said freely moveable means and said hollow element induces a voltage in said coil.

6. A pacemaker as claimed in claim 5, wherein said magnetic dipole is formed by solid permanent magnetic material.

7. A pacemaker as claimed in claim 5, wherein said magnetic dipole is formed by powder magnetic material.

8. A pacemaker as claimed in claim 7, wherein said magnetic dipole has an outer layer covering said powder magnetic material.

9. A pacemaker as claimed in claim 1, wherein said freely moveable means constitutes a plurality of electrically conductive particles, and wherein said means for detecting constitutes a pair of spaced electrodes disposed in said hollow element and adapted for connection to a voltage source such that relative movement between said particles and said hollow element changes the resistance between said electrodes.

10. A pacemaker as claimed in claim 1, wherein said hollow element has an interior surface and wherein said interior surface and said freely moveable means consist of respective materials such that said relative movement generates an acoustic signal, and wherein said means for generating an electric signal is a microphone disposed for receiving said acoustic signal.

11. A pacemaker as claimed in claim 10, wherein said interior surface consists of a plurality of different materials having respectively different hardnesses.

12. A pacemaker as claimed in claim 10, wherein said interior structured surface has at least a portion thereof with a structured surface.

13. A pacemaker as claimed in claim 10, wherein said interior surface is smooth.

14. A pacemaker as claimed in claim 1, wherein said hollow element has an interior surface, and wherein at least one of said interior surface or said freely moveable means is spherical.

15. A pacemaker as claimed in claim 1, wherein said hollow element has an interior surface, and wherein at least one of said interior surface or said freely moveable means is a regular polyhedron.

16. A pacemaker as claimed in claim 1, wherein said hollow element is an ellipsoid.

17. A pacemaker as claimed in claim 1, wherein at least said hollow element has a composition selected such that said relative movement causes interaction with said freely moveable means which is different for different directions of movement of said hollow element.

18. A pacemaker as claimed in claim 1, wherein at least said hollow element has a selectively structured surface such that said relative movement causes interaction with said freely moveable means which is different for different directions of movement of said hollow element.

19. A pacemaker as claimed in claim 1, further comprising a fluid filling said hollow element of selected density and viscosity.

20. A pacemaker as claimed in claim 1, wherein said freely moveable means comprises a plurality of particles.

21. A pacemaker as claimed in claim 20, wherein said particles are electrically conductive, and wherein said means for generating an electrical signal includes two spaced electrodes disposed inside said hollow element with said particles at least partially therebetween, said electrodes adapted for connection to a voltage source, such that movement of said hollow element causes said particles to re-orient within said hollow element thereby changing the resistance between said electrodes.

22. A pacemaker as claimed in claim 21, wherein said hollow element is a cube, and wherein said electrodes are disposed on one pair of opposite faces of said cube.

23. A pacemaker as claimed in claim 21, wherein said hollow element is a sphere, and wherein aid electrodes are C-shaped electrodes disposed within said sphere.

24. A pacemaker implantable in a patient for stimulating the heart of said patient comprising:
   a hollow element having an interior surface;
   a freely moveable element enclosed in said hollow element for generating an acoustic signal by mechanically interacting with said interior surface of said hollow element due to movement of said patient and said hollow element;

a microphone for receiving said acoustic signal and generating an electrical signal therefrom at least partially proportional to the mechanical interaction of said hollow element and said freely moveable element; and means for generating stimulation pulses for stimulating said heart at a stimulation frequency including means responsive to said electrical signal for varying said stimulation frequency dependent on said physical activity of said patient.

25. A pacemaker as claimed in claim 24, wherein at least one of said interior surface or said freely moveable element is facetted.

26. A pacemaker as claimed in claim 24, wherein at least one of said interior surface or said hollow element is spherical.

27. A pacemaker as claimed in claim 24, wherein at least one of said interior surface or said hollow element is a regular polyhedron.

28. A pacemaker as claimed in claim 24, further comprising:

a threshold circuit connected to said microphone to which said electrical signal is supplied; and a pulse shaper means connected to an output of said threshold circuit, for generating pulses of uniform duration and amplitude from the output of said threshold circuit.

29. A pacemaker implantable in a patient for stimulating the heart of said patient comprising:

a hollow element;

a freely moveable magnetic dipole enclosed in said hollow element, said magnetic dipole changing position within said hollow element upon movement of said patient and said hollow element;

at least one coil at least partially surrounding said hollow element in which voltage is induced by movement of said magnetic dipole within said hollow element; and means for generating stimulation pulses for stimulating said heart at a stimulation frequency including means responsive to said electrical signal for varying said stimulation frequency dependent on said physical activity of said patient.

30. A pacemaker implantable in a patient for stimulating the heart of said patient comprising:

a hollow element;

a plurality of electrical conducting particles enclosed in said hollow element and freely moveable therein such that said particles re-orient within said hollow element upon a change in position of said hollow element due to movement of said patient;

a pair of spaced electrodes within said hollow element adapted for connection to a voltage source, said particles being at least partially disposed between said electrodes and changing the resistance between said electrodes upon re-orientation of said particles due to movement of said patient; and means for generating stimulation pulsed for stimulating said heart at a stimulation frequency including means responsive to said electrical signal for varying said stimulation frequency dependent on said physical activity of said patient.

31. A pacemaker as claimed in claim 30, wherein said hollow element is a sphere, and wherein said electrodes are C-shaped electrodes disposed within said sphere.

32. A pacemaker as claimed in claim 31, wherein said electrodes are respectively disposed in perpendicular planes.

33. A pacemaker as claimed in claim 30, wherein said hollow element is a cube, and wherein said electrodes are disposed on a pair of opposite faces of said cube.

* * * * *